(12) United States Patent
Rasmussen et al.

(10) Patent No.: US 11,700,493 B2
(45) Date of Patent: Jul. 11, 2023

(54) HEARING AID COMPRISING A LEFT-RIGHT LOCATION DETECTOR

(71) Applicant: Oticon A/S, Smørum (DK)

(72) Inventors: Karsten Bo Rasmussen, Smørum (DK); Svend Oscar Petersen, Smørum (DK); Troels Holm Pedersen, Copenhagen (DK); Amalie Sofie Ekstrand, Smørum (DK); Anders Vinther Olsen, Smørum (DK); Jacob Lindvig, Smørum (DK); Jana Thorin, Smørum (DK); Michael Syskind Pedersen, Smørum (DK); Nicolai Westergren, Smørum (DK); Sudershan Y. S, Smørum (DK); Tanveer Bhuiyan, Smørum (DK); Svend Feldt, Ballerup (DK)

(73) Assignee: Oticon A/S, Smørum (DK)

( * ) Notice: Subject to any disclaimer, the term of this patent is extended or adjusted under 35 U.S.C. 154(b) by 0 days.

(21) Appl. No.: 17/319,384

(22) Filed: May 13, 2021

(65) Prior Publication Data
US 2021/0360354 A1 Nov. 18, 2021

(30) Foreign Application Priority Data
May 14, 2020 (EP) .................................. 20174648

(51) Int. Cl.
*H04R 25/00* (2006.01)
(52) U.S. Cl.
CPC .......... *H04R 25/407* (2013.01); *H04R 25/552* (2013.01); *H04R 25/554* (2013.01); *H04R 2225/025* (2013.01)

(58) Field of Classification Search
CPC .......... H04R 2225/025; H04R 2225/61; H04R 25/407; H04R 25/552; H04R 25/554
USPC ....................................................... 381/313
See application file for complete search history.

(56) References Cited

U.S. PATENT DOCUMENTS

| 10,460,095 | B2 * | 10/2019 | Boesen ................ H04R 1/1041 |
| 2013/0279724 | A1 | 10/2013 | Stafford et al. |
| 2014/0051939 | A1 | 2/2014 | Messerschmidt |
| 2017/0230754 | A1 | 8/2017 | Dusan |
| 2019/0174238 | A1 | 6/2019 | Lunner et al. |
| 2019/0297431 | A1 | 9/2019 | Oesch et al. |

FOREIGN PATENT DOCUMENTS

| EP | 2 293 589 A1 | 3/2011 |
| EP | 2 991 380 A1 | 3/2016 |
| EP | 3 709 115 A1 | 9/2020 |
| WO | WO 2014/092932 A1 | 6/2014 |

OTHER PUBLICATIONS

Extended European Search Report for European Application No. 21173042.9, dated Oct. 28, 2021.

* cited by examiner

*Primary Examiner* — Phylesha Dabney
(74) *Attorney, Agent, or Firm* — Birch, Stewart, Kolasch & Birch, LLP (57) ABSTRACT

A hearing aid is configured to be located at or in an ear of a user. The hearing aid comprises a heartbeat detector providing a pulse control signal, and a processor. The processor is configured to estimate whether the hearing aid is located at a left or a right ear of the user in dependence of the pulse control signal. A method of operating a hearing aid and a binaural hearing aid system is further disclosed.

18 Claims, 5 Drawing Sheets

HEARING AID COMPRISING A LEFT-RIGHT LOCATION DETECTOR

SUMMARY

Figure 1:
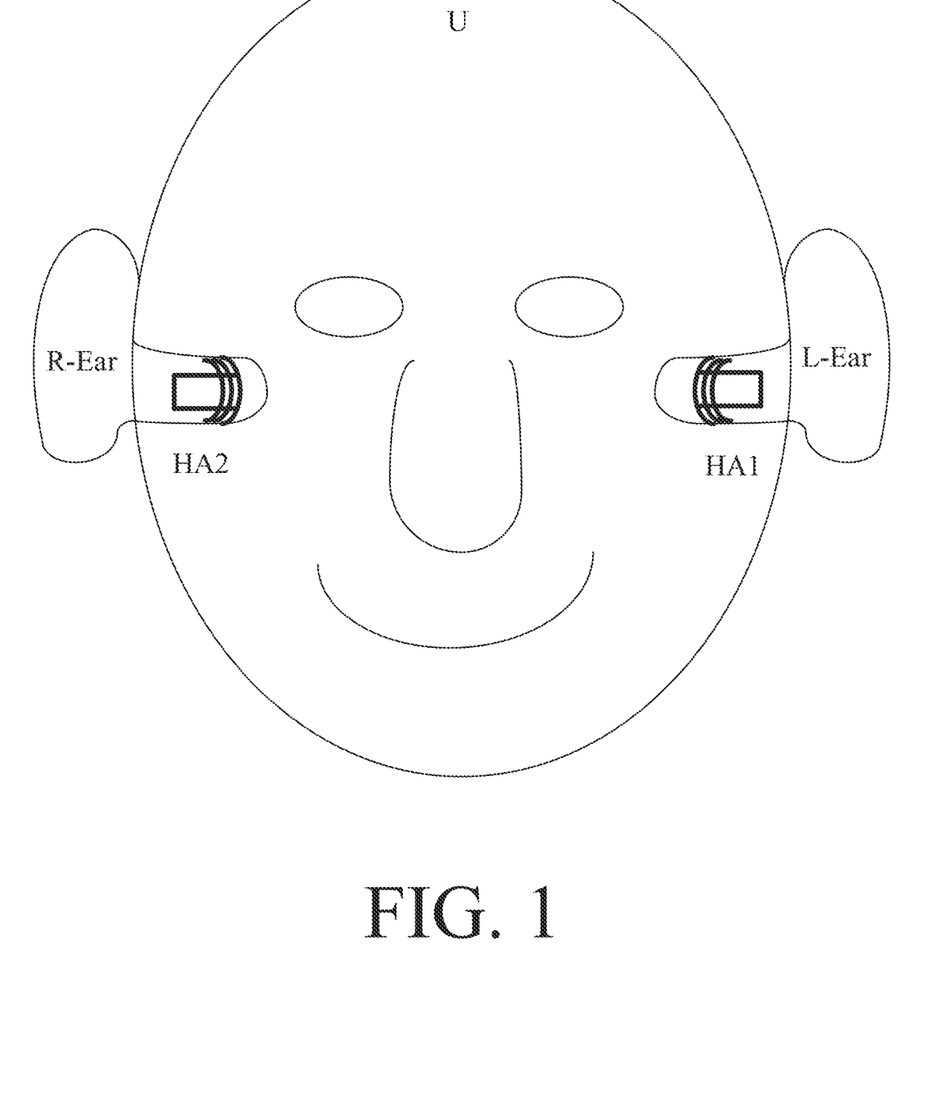
FIG. 1 shows a hearing system comprising two identically looking (or close to identically looking) hearing instruments located in the respective ear canals of a user, FIG. 2A schematically illustrates a hearing system as shown in FIG. 1 also showing the users heart and schematic blood paths from the heart to the ears of the user.

The present application relates to hearing devices, e.g. hearing aids (here also termed hearing instruments), configured to be located in or at each ear, as shown in FIG. 1. A hearing system, e.g. a binaural hearing aid system, may comprise first and second hearing devices configured to be located at or in left and right ears, respectively, of a user (e.g. a specific user, e.g. a user having a hearing impairment). If the hearing instruments look identical (e.g. are identical in form and colour, etc.), the instrument intended for a left side may be mounted on the right ear and the instrument intended for the right side may be mounted at the left side. Hereby sound intended for the left ear may be presented to the right ear and vice versa. Today this can be solved e.g. by marking the instruments with an "L" and an "R" (or a colour code, etc.). Still, a user may confuse the two devices. A more elegant way to cope with the problem would be to automatically determine in which ear each hearing instrument is mounted. Hereby the user does not have to think about mounting the device in a specific ear, which is especially advantageous, if (the outer appearance of) the instruments are identical (or identical 'at first sight').

The present concept may in particular be relevant in devices, such as e.g. hearing aids, where settings (of processing parameters. e.g. gain) in the two hearing instruments (configured to be located at left and right ears) are different. In this case it is beneficial know whether a given hearing instrument is located at a left or a right ear. In other applications. e.g. for earpieces of an audio delivery device, or a hearing aid) it may be useful in certain situations to identify whether mono signals should be provided rather than stereo. This may e.g. be relevant if it is believed that the measured heartbeat of the respective earpieces originate from two different hearts (i.e. different persons wearing the two instruments (earpieces), for sharing audio).

EP2991380A1 addresses the same problem. EP2991380A1 proposes to estimate the location of the hearing instrument based on spatial location of an identification signal. Such scheme requires manual action, whereas the scheme proposed in the present disclosure (after an initial setup) may work automatically.

A Hearing Aid:

In an aspect of the present application, a hearing aid configured to be located at or in an ear of a user is provided. The hearing aid comprises a heartbeat detector providing a pulse control signal, and a processor. The processor may be configured to estimate whether the hearing aid is located at a left or a right ear of the user in dependence of said pulse control signal.

Thereby an improved hearing aid comprising a left-right location detector may be provided.

The hearing aid may comprise a memory wherein respective reference values of the pulse control signal (or data derived therefrom) characteristic of a left and right and right hearing aid (when located at left and right ears of the user, e.g. measured in a fitting session) are stored. The processor may be configured to compare a current pulse control signal (or data derived therefrom) with the reference pulse control signals (or data derived therefrom). Thereby a given hearing aid may identify whether it is intentionally mounted at a left or right ear of the user (in dependence of a comparison measure being smaller than a threshold).

The hearing aid may comprise transceiver circuitry configured to establish a communication link to another device. The 'another device' may e.g. be another hearing aid of a binaural hearing aid system or an auxiliary device, e.g. a remote control device, e.g. a smartphone or the like.

The heartbeat detector may be configured to provide that the pulse control signal comprises a time dependent waveform of the heartbeat of the user. The heartbeat detector may thus provide the pulse control signal as (an analogue or digitized) amplitude versus time.

The processor may be configured to transmit the pulse control signal to another device. The pulse control signal may be transmitted via the communication link. The hearing device may be configured to receive a pulse control signal from another device (e.g. from the 'another device'). The 'another device' may e.g. be another hearing aid of a binaural hearing aid system or an auxiliary device, e.g. a remote control device, e.g. a smartphone or the like.

The heartbeat detector may e.g. comprise a microphone (e.g. an in-ear-microphone), a movement sensor, or a PPG sensor. The microphone may be a microphone facing the eardrum when the hearing aid is mounted on the user. The microphone may be a bone conduction microphone. The movement sensor may comprise an accelerometer. The PPG (Photoplethysmography) sensor may comprise a pulse oximetry sensor as well as a heartbeat sensor.

The processor may be configured to automatically select appropriate processing parameters in dependence of said pulse control signals. The hearing aid may e.g. comprise a memory storing processing parameters (settings) for the relevant processing algorithms that deviate from the left to the right ear of the user (e.g. corresponding to different hearing impairments at left and right ears of the user). Thereby the appropriate parameters settings can be chosen and used in any of the first and second hearing aids irrespective whether they are mounted at the left or right hears of the user.

When the side (left or right for a given device has been determined, the side-dependent settings (processing parameters) can be set in each device. Side dependent settings may e.g. be

- Correct side while playing music, movie playback, or gaming.
- 3D rendering, e.g. 7.1 downmix.
- Correct positioning of sound sources in augmented hearing.
- Hearing loss compensation gain.
- User interface, e.g. volume up by tapping left device, volume down by tapping right device
- Sound Direction-of-arrival estimation.

The processor may be configured to issue an alarm (e.g. a warning or recommendation) in case that the first and second hearing aids are not located at their appropriate ears. The processor may be configured to inform the user (or other person) in case that the first and second hearing aids are not located at their appropriate ears. The hearing aid may e.g. instruct the user to swap the first and second hearing aids between the ears of the user. Such alarm or information of instruction may e.g. be provided via a user interface, an audio and/or visual interface, e.g. via a loudspeaker of the hearing devices, or a remote control, and/or a smartphone, etc.

The hearing aid may be configured to monitor changes in timing of the pulse control signal. The hearing aid may be configured to monitor changes in timing between the pulse control signals of the hearing device and the other device (e.g. between first and second devices, e.g. hearing aids, of a binaural hearing system, e.g. a binaural hearing aid system). Based on the changes, it may be determined whether the user's head it turned to either left, right or pointing forward. The time delay may be slightly changed when the head is turned from one position to another. The hearing aid may be configured to store changes over time. The hearing aid may comprise a memory that stores the time delay differences over time.

Differences in time-of-arrival of acoustic signals (audio data) at the left and right ears depend on the direction-of-arrival (DOA), but are generally less than 1 ms (e.g. 0.5 ms). Differences in the 'time-of-arrival' of heartbeats at the left and right ears are different from person to person, but are generally in the range of 5-10 ms (cf. ΔD in FIG. 2B). Hence, the audio data may be used to synchronize pulse data (accelerometer data). Thereby a separate synchronization may be dispensed with.

The processing time for estimating whether the hearing aid is located at the left or right ear may vary according to the kind of heartbeat detector used. A processing time of 30 s or more (from the initiation of the procedure) may be experienced. In case, processing parameters of the hearing aid are (very) different, e.g. due to (very) different hearing losses of the left and right ears of the user, a default configuration may be loaded and used until the present left-right side situation has been detected (if the determined left-right configuration of the hearing instruments is contrary to the intention, the instruments should switch side, e.g. issuing a warning/recommendation (e.g. as an acoustic indication via the loudspeakers of the respective hearing aids, or as an information presented to the user via a user interface, e.g. via an APP of a smartphone, tablet or other appropriate device).

The hearing aid may be configured to only estimate whether said hearing aid is located at a left or a right ear of the user, when a specific criterion is fulfilled. Various efforts may be added to make the pulse measurement more reliable. The specific criterion may e.g. relate to reliability of the pulse control signal. The specific criterion may e.g. comprise a logic combination of control signals from one or more sensors. The specific criterion may e.g. comprise that the user is not moving, or that the user is not talking, or that the background noise is not above a specified level, or a combination thereof.

The hearing aid may be constituted by or comprise an air-conduction type hearing aid, a bone-conduction type hearing aid, a cochlear implant type hearing aid, or a combination thereof.

The hearing aid may be adapted to provide a frequency dependent gain and/or a level dependent compression and/or a transposition (with or without frequency compression) of one or more frequency ranges to one or more other frequency ranges, e.g. to compensate for a hearing impairment of a user. The hearing aid may comprise a signal processor for enhancing the input signals and providing a processed output signal.

The hearing aid may comprise an output unit for providing a stimulus perceived by the user as an acoustic signal based on a processed electric signal. The output unit may comprise a number of electrodes of a cochlear implant (for a CI type hearing aid) or a vibrator of a bone conducting hearing aid. The output unit may comprise an output transducer. The output transducer may comprise a receiver (loudspeaker) for providing the stimulus as an acoustic signal to the user (e.g. in an acoustic (air conduction based) hearing aid). The output transducer may comprise a vibrator for providing the stimulus as mechanical vibration of a skull bone to the user (e.g. in a bone-attached or bone-anchored hearing aid).

The hearing aid may comprise an input unit for providing an electric input signal representing sound. The input unit may comprise an input transducer, e.g. a microphone, for converting an input sound to an electric input signal. The input unit may comprise a wireless receiver for receiving a wireless signal comprising or representing sound and for providing an electric input signal representing said sound. The wireless receiver may e.g. be configured to receive an electromagnetic signal in the radio frequency range (3 kHz to 300 GHz). The wireless receiver may e.g. be configured to receive an electromagnetic signal in a frequency range of light (e.g. infrared light 300 GHz to 430 THz, or visible light. e.g. 430 THz to 770 THz).

The hearing aid may comprise antenna and transceiver circuitry (e.g. a wireless receiver) for wirelessly receiving a direct electric input signal from another device, e.g. from an entertainment device (e.g. a TV-set), a communication device, a wireless microphone, or another hearing aid. The direct electric input signal may represent or comprise an audio signal and/or a control signal and/or an information signal. The hearing aid may comprise demodulation circuitry for demodulating the received direct electric input to provide the direct electric input signal representing an audio signal and/or a control signal e.g. for setting an operational parameter (e.g. volume) and/or a processing parameter of the hearing aid. In general, a wireless link established by antenna and transceiver circuitry of the hearing aid can be of any type. The wireless link may be established between two devices. e.g. between an entertainment device (e.g. a TV) and the hearing aid, or between two hearing aids, e.g. via a third, intermediate device (e.g. a processing device, such as a remote control device, a smartphone, etc.). The wireless link may be used under power constraints, e.g. in that the hearing aid may be constituted by or comprise a portable (typically battery driven) device. The wireless link may be a link based on near-field communication, e.g. an inductive link based on an inductive coupling between antenna coils of transmitter and receiver parts. The wireless link may be based on far-field, electromagnetic radiation. The communication via the wireless link may be arranged according to a specific modulation scheme, e.g. an analogue modulation scheme, such as FM (frequency modulation) or AM (amplitude modulation) or PM (phase modulation), or a digital modulation scheme, such as ASK (amplitude shift keying). e.g. On-Off keying, FSK (frequency shift keying), PSK (phase shift keying), e.g. MSK (minimum shift keying), or QAM (quadrature amplitude modulation), etc.

The communication between the hearing aid and the other device may be in the base band (audio frequency range, e.g. between 0 and 20 kHz). Preferably, communication between the hearing aid and the other device is based on some sort of modulation at frequencies above 100 kHz. Preferably, frequencies used to establish a communication link between the hearing aid and the other device is below 70 GHz, e.g. located in a range from 50 MHz to 70 GHz, e.g. above 300 MHz, e.g. in an ISM range above 300 MHz, e.g. in the 900 MHz range or in the 2.4 GHz range or in the 5.8 GHz range or in the 60 GHz range (ISM=Industrial, Scientific and Medical, such standardized ranges being e.g. defined by the International Telecommunication Union, ITU). The wireless link may be based on a standardized or proprietary technology. The wireless link may be based on Bluetooth technology (e.g. Bluetooth Low-Energy technology), or Ultra WideBand technology (UWB).

The hearing aid may be or form part of a portable (i.e. configured to be wearable) device. e.g. a device comprising a local energy source, e.g. a battery, e.g. a rechargeable battery. The hearing aid may e.g. be a low weight, easily wearable, device, e.g. having a total weight less than 100 g, e.g. less than 20 g.

The hearing aid may comprise a forward or signal path between an input unit (e.g. an input transducer, such as a microphone or a microphone system and/or direct electric input (e.g. a wireless receiver)) and an output unit, e.g. an output transducer. The signal processor may be located in the forward path. The signal processor may be adapted to provide a frequency dependent gain according to a user's particular needs. The hearing aid may comprise an analysis path comprising functional components for analyzing the input signal (e.g. determining a level, a modulation, a type of signal, an acoustic feedback estimate, etc.). Some or all signal processing of the analysis path and/or the signal path may be conducted in the frequency domain. Some or all signal processing of the analysis path and/or the signal path may be conducted in the time domain.

An analogue electric signal representing an acoustic signal may be converted to a digital audio signal in an analogue-to-digital (AD) conversion process, where the analogue signal is sampled with a predefined sampling frequency or rate $f_s$, $f_s$ being e.g. in the range from 8 kHz to 48 kHz (adapted to the particular needs of the application) to provide digital samples $x_n$ (or x[n]) at discrete points in time $t_n$ (or n), each audio sample representing the value of the acoustic signal at $t_n$ by a predefined number $N_b$ of bits, $N_b$ being e.g. in the range from 1 to 48 bits, e.g. 24 bits. Each audio sample is hence quantized using $N_b$ bits (resulting in $2^{Nb}$ different possible values of the audio sample). A digital sample x has a length in time of $1/f_s$, e.g. 50 µs, for $f_s$=20 kHz. A number of audio samples may be arranged in a time frame. A time frame may comprise 64 or 128 audio data samples. Other frame lengths may be used depending on the practical application.

The hearing aid may comprise an analogue-to-digital (AD) converter to digitize an analogue input (e.g. from an input transducer, such as a microphone) with a predefined sampling rate, e.g. 20 kHz. The hearing aids may comprise a digital-to-analogue (DA) converter to convert a digital signal to an analogue output signal. e.g. for being presented to a user via an output transducer.

The hearing aid, e.g. the input unit, and or the antenna and transceiver circuitry comprise(s) a TF-conversion unit for providing a time-frequency representation of an input signal. The time-frequency representation may comprise an array or map of corresponding complex or real values of the signal in question in a particular time and frequency range. The TF conversion unit may comprise a filter bank for filtering a (time varying) input signal and providing a number of (time varying) output signals each comprising a distinct frequency range of the input signal. The TF conversion unit may comprise a Fourier transformation unit for converting a time variant input signal to a (time variant) signal in the (time-) frequency domain. The frequency range considered by the hearing aid from a minimum frequency $f_{min}$ to a maximum frequency $f_{max}$ may comprise a part of the typical human audible frequency range from 20 Hz to 20 kHz. e.g. a part of the range from 20 Hz to 12 kHz. Typically, a sample rate $f_s$ is larger than or equal to twice the maximum frequency $f_{max}$, $f_s \geq 2f_{max}$. A signal of the forward and/or analysis path of the hearing aid may be split into a number NI of frequency bands (e.g. of uniform width), where NI is e.g. larger than 5, such as larger than 10, such as larger than 50, such as larger than 100, such as larger than 500, at least some of which are processed individually. The hearing aid may be adapted to process a signal of the forward and/or analysis path in a number NP of different frequency channels (NP≤NI). The frequency channels may be uniform or non-uniform in width (e.g. increasing in width with frequency), overlapping or non-overlapping.

The hearing aid may be configured to operate in different modes, e.g. a normal mode and one or more specific modes, e.g. selectable by a user, or automatically selectable. A mode of operation may be optimized to a specific acoustic situation or environment. A mode of operation may include a low-power mode, where functionality of the hearing aid is reduced (e.g. to save power). e.g. to disable wireless communication, and/or to disable specific features of the hearing aid.

The hearing aid may comprise a number of detectors configured to provide status signals relating to a current physical environment of the hearing aid (e.g. the current acoustic environment), and/or to a current state of the user wearing the hearing aid, and/or to a current state or mode of operation of the hearing aid. Alternatively, or additionally, one or more detectors may form part of an external device in communication (e.g. wirelessly) with the hearing aid. An external device may e.g. comprise another hearing aid, a remote control, and audio delivery device, a telephone (e.g. a smartphone), an external sensor, etc.

One or more of the number of detectors may operate on the full band signal (time domain). One or more of the number of detectors may operate on band split signals ((time-) frequency domain). e.g. in a limited number of frequency bands.

The number of detectors may comprise a level detector for estimating a current level of a signal of the forward path. The detector may be configured to decide whether the current level of a signal of the forward path is above or below a given (L-)threshold value. The level detector operates on the full band signal (time domain). The level detector operates on band split signals ((time-) frequency domain).

The hearing aid may comprise a voice activity detector (VAD) for estimating whether or not (or with what probability) an input signal comprises a voice signal (at a given point in time). A voice signal may in the present context be taken to include a speech signal from a human being. It may also include other forms of utterances generated by the human speech system (e.g. singing). The voice activity detector unit may be adapted to classify a current acoustic environment of the user as a VOICE or NO-VOICE environment. This has the advantage that time segments of the electric microphone signal comprising human utterances (e.g. speech) in the user's environment can be identified, and thus separated from time segments only (or mainly) comprising other sound sources (e.g. artificially generated noise). The voice activity detector may be adapted to detect as a VOICE also the user's own voice. Alternatively, the voice activity detector may be adapted to exclude a user's own voice from the detection of a VOICE.

The hearing aid may comprise an own voice detector for estimating whether or not (or with what probability) a given input sound (e.g. a voice, e.g. speech) originates from the voice of the user of the system. A microphone system of the hearing aid may be adapted to be able to differentiate between a user's own voice and another person's voice and possibly from NON-voice sounds. Side detection may be disabled during own voice, as pulse may be more difficult to detect during own voice. Side detection refers to detecting if the instrument is located on left or right side of the head—or the two instruments have been swapped.

The number of detectors may comprise a movement detector, e.g. an acceleration sensor. The movement detector may be configured to detect movement of the user's facial muscles and/or bones, e.g. due to speech or chewing (e.g. jaw movement) and to provide a detector signal indicative thereof.

The hearing aid may comprise a classification unit configured to classify the current situation based on input signals from (at least some of) the detectors, and possibly other inputs as well. In the present context 'a current situation' may be taken to be defined by one or more of a) the physical environment (e.g. including the current electromagnetic environment. e.g. the occurrence of electromagnetic signals (e.g. comprising audio and/or control signals) intended or not intended for reception by the hearing aid, or other properties of the current environment than acoustic);

b) the current acoustic situation (input level, feedback, etc.), and c) the current mode or state of the user (movement, temperature, cognitive load, etc.);

d) the current mode or state of the hearing aid (program selected, time elapsed since last user interaction, etc.) and/or of another device in communication with the hearing aid.

The classification unit may be based on or comprise a neural network, e.g. a trained neural network.

The hearing aid may further comprise other relevant functionality for the application in question, e.g. compression, noise reduction, feedback control, etc.

The monitoring of a user's heartbeat according to the present disclosure may e.g. be performed continuously. Another option may be (e.g. for power saving purposes), to turn off the heartbeat detector (or one of the heartbeat detectors) after a correct side has been established. Yet another option may be that the heartbeat detector, during an initial phase, performs at a relatively high sample rate until the correct side has been established, whereafter a relatively low sample rate (or whereafter the heartbeat detector enters a low-power mode). The heartbeat detector may e.g. be activated during a power-on procedure to verify whether a given hearing instrument is located at the ear it is intended for (and otherwise be in a lower-power mode, where heartbeat is monitored at a lower sampling rate, e.g. for health monitoring or sports purposes).

The hearing aid may comprise a hearing instrument, e.g. a hearing instrument adapted for being located at the ear or fully or partially in the ear canal of a user, e.g. a headset, an earphone, an ear protection device or a combination thereof. The hearing assistance system may comprise a speakerphone (comprising a number of input transducers and a number of output transducers, e.g. for use in an audio conference situation), e.g. comprising a beamformer filtering unit, e.g. providing multiple beamforming capabilities.

In a further aspect, a first hearing aid configured to be located at or in a first ear of a user is provided. The first hearing aid may comprise a heartbeat detector providing a first pulse control signal indicative of a time variation of the user's heartbeat at the first ear of the user, and a processor. The first hearing aid may be configured to receive a second pulse control signal from a second hearing aid, the second hearing aid being configured to be located at a second ear of the user, wherein the second pulse control signal is indicative of a time variation of the user's heartbeat at the second ear of the user. The processor may be configured to estimate whether the hearing aid is located at a left or a right ear of the user in dependence of the first pulse control signal and the second pulse control signal.

Use:

In an aspect, use of a hearing aid as described above, in the 'detailed description of embodiments' and in the claims, is moreover provided. Use may be provided in a system comprising audio distribution. Use may be provided in a system comprising one or more hearing aids (e.g. hearing instruments). e.g. a binaural hearing aid system, headsets, ear phones, active ear protection systems, etc.

A Method:

In an aspect, method of operating a (first) hearing aid configured to be located at or in a first ear of a user is furthermore provided by the present application. The method comprises providing a first pulse control signal indicative of a time variation of the user's heartbeat at the ear of the user. The method may comprise estimating whether the (first) hearing aid is located at a left or a right ear of the user in dependence of said first pulse control signal.

It is intended that some or all of the structural features of the device described above, in the 'detailed description of embodiments' or in the claims can be combined with embodiments of the method, when appropriately substituted by a corresponding process and vice versa. Embodiments of the method have the same advantages as the corresponding devices.

The method may comprise
   receiving a second pulse control signal (in said first hearing aid) from a second hearing aid configured to be located at a second ear of the user, and
   estimating whether the (first) hearing aid is located at a left or a right ear of the user in dependence of the first and second pulse control signals.

The method may comprise
   transmitting the first pulse control signal (from the first hearing aid) to a second hearing aid configured to be located at a second ear of the user.

The pulse measurements may be exchanged between the first and second hearing aids, e.g. via a third (intermediate, e.g. processing) device. The method may comprise receiving a second pulse control signal from a second hearing aid configured to be located at a second ear of the user. The comparison of the first and second pulse control signals may be performed in the hearing aid(s) or in a third device, and the result (the intended location of a given hearing aid) communicated to the (respective) first and second hearing aids.

The method may comprise
   providing that the determination of whether the hearing aid is located at a left or a right ear of the user is performed in a separate device in communication with the hearing aid.

In a further aspect, a method of operating a hearing aid configured to be located at or in a first ear of a user is provided. The method may comprise
   providing a first pulse control signal indicative of a time variation of the user's heartbeat at the first ear of the user, and
   receiving a second pulse control signal from a second hearing aid configured to be located at a second ear of the user, wherein the second pulse control signal is indicative of a time variation of said user's heartbeat at the second ear of the user, and
   estimating whether the hearing aid is located at a left or a right ear of the user in dependence of the first and second pulse control signals.

A Computer Readable Medium or Data Carrier:

In an aspect, a tangible computer-readable medium (a data carrier) storing a computer program comprising program code means (instructions) for causing a data processing system (a computer) to perform (carry out) at least some (such as a majority or all) of the (steps of the) method described above, in the 'detailed description of embodiments' and in the claims, when said computer program is executed on the data processing system is furthermore provided by the present application.

By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Disk and disc, as used herein, includes compact disc (CD), laser disc, optical disc, digital versatile disc (DVD), floppy disk and Blu-ray disc where disks usually reproduce data magnetically, while discs reproduce data optically with lasers. Other storage media include storage in DNA (e.g. in synthesized DNA strands). Combinations of the above should also be included within the scope of computer-readable media. In addition to being stored on a tangible medium, the computer program can also be transmitted via a transmission medium such as a wired or wireless link or a network, e.g. the Internet. and loaded into a data processing system for being executed at a location different from that of the tangible medium.

A Computer Program:

A computer program (product) comprising instructions which, when the program is executed by a computer, cause the computer to carry out (steps of) the method described above, in the 'detailed description of embodiments' and in the claims is furthermore provided by the present application.

A Data Processing System:

In an aspect, a data processing system comprising a processor and program code means for causing the processor to perform at least some (such as a majority or all) of the steps of the method described above, in the 'detailed description of embodiments' and in the claims is furthermore provided by the present application.

A Binaural Hearing Aid System:

In a further aspect, a binaural hearing aid system comprising first and second hearing aids as described above, in the 'detailed description of embodiments', and in the claims, is moreover provided.

The binaural hearing system may be configured to exchange the pulse control signals between them. The binaural hearing aid system may be configured to exchange the pulse control signals between them in dependence of a trigger event. A trigger event may e.g. be a power up of the first and second hearing aids of the binaural hearing aid system. A trigger event may e.g. be a request from a user interface.

In a further aspect, a hearing system comprising a hearing aid as described above, in the 'detailed description of embodiments', and in the claims, AND an auxiliary device is moreover provided.

The hearing system may be adapted to establish a communication link between the hearing aid and the auxiliary device to provide that information (e.g. control and status signals, possibly audio signals) can be exchanged or forwarded from one to the other.

The auxiliary device may comprise a remote control, a smartphone, or other portable or wearable electronic device, such as a smartwatch or the like.

The auxiliary device may be constituted by or comprise a remote control for controlling functionality and operation of the hearing aid(s). The function of a remote control may be implemented in a smartphone, the smartphone possibly running an APP allowing to control the functionality of the audio processing device via the smartphone (the hearing aid(s) comprising an appropriate wireless interface to the smartphone, e.g. based on Bluetooth or some other standardized or proprietary scheme).

The auxiliary device may be constituted by or comprise an audio gateway device adapted for receiving a multitude of audio signals (e.g. from an entertainment device, e.g. a TV or a music player, a telephone apparatus, e.g. a mobile telephone or a computer, e.g. a PC) and adapted for selecting and/or combining an appropriate one of the received audio signals (or combination of signals) for transmission to the hearing aid.

The auxiliary device may be constituted by or comprise another hearing aid. The hearing system may comprise two hearing aids adapted to implement a binaural hearing system, e.g. a binaural hearing aid system. The binaural hearing aid system may comprise first and second hearing aids according as described above, in the 'detailed description of embodiments', and in the claims. The first and second hearing aids of the binaural hearing aid system may be configured to exchange the respective pulse control signals between them. The binaural hearing aid system may be configured to exchange the pulse control signals between them in dependence of a trigger event. A trigger event may e.g. be a power up of the first and second hearing aids of the binaural hearing aid system. A trigger event may e.g. be a request from a user interface.

The determination of whether a given one of the first and second hearing aids is located at a left or a right ear of the user in dependence of the first and second pulse control signals may be performed in an external processing device, e.g. the auxiliary device (e.g. handled by a user interface, e.g. implemented as an APP, of a smartphone or other portable device). Thereby, only the respective first and second pulse control signals (cf. e.g. signals $HB_1$, $HB_2$ in FIG. 5) and the respective resulting first and second control signals (cf. e.g. signals $RL_{ctr,1}$, $RL_{ctr,2}$ in FIG. 5) are exchanged between the first and second hearing aids and the external processing device.

An APP:

In a further aspect, a non-transitory application, termed an APP, is furthermore provided by the present disclosure. The APP comprises executable instructions configured to be executed on an auxiliary device to implement a user interface for a hearing aid or a hearing system described above in the 'detailed description of embodiments', and in the claims. The APP may be configured to run on cellular phone, e.g. a smartphone, or on another portable device allowing communication with said hearing aid or said hearing system.

Definitions

In the present context, a hearing aid. e.g. a hearing instrument, refers to a device, which is adapted to improve, augment and/or protect the hearing capability of a user by receiving acoustic signals from the user's surroundings, generating corresponding audio signals, possibly modifying the audio signals and providing the possibly modified audio signals as audible signals to at least one of the user's ears.

Such audible signals may e.g. be provided in the form of acoustic signals radiated into the user's outer ears, acoustic signals transferred as mechanical vibrations to the user's inner ears through the bone structure of the user's head and/or through parts of the middle ear as well as electric signals transferred directly or indirectly to the cochlear nerve of the user.

The hearing aid may be configured to be worn in any known way, e.g. as a unit arranged behind the ear with a tube leading radiated acoustic signals into the ear canal or with an output transducer, e.g. a loudspeaker, arranged close to or in the ear canal, as a unit entirely or partly arranged in the pinna and/or in the ear canal, as a unit, e.g. a vibrator, attached to a fixture implanted into the skull bone, as an attachable, or entirely or partly implanted, unit, etc. The hearing aid may comprise a single unit or several units communicating (e.g. acoustically, electrically or optically) with each other. The loudspeaker may be arranged in a housing together with other components of the hearing aid, or may be an external unit in itself (possibly in combination with a flexible guiding element, e.g. a dome-like element).

More generally, a hearing aid comprises an input transducer for receiving an acoustic signal from a user's surroundings and providing a corresponding input audio signal and/or a receiver for electronically (i.e. wired or wirelessly) receiving an input audio signal, a (typically configurable) signal processing circuit (e.g. a signal processor, e.g. comprising a configurable (programmable) processor, e.g. a digital signal processor) for processing the input audio signal and an output unit for providing an audible signal to the user in dependence on the processed audio signal. The signal processor may be adapted to process the input signal in the time domain or in a number of frequency bands. In some hearing aids, an amplifier and/or compressor may constitute the signal processing circuit. The signal processing circuit typically comprises one or more (integrated or separate) memory elements for executing programs and/or for storing parameters used (or potentially used) in the processing and/or for storing information relevant for the function of the hearing aid and/or for storing information (e.g. processed information, e.g. provided by the signal processing circuit), e.g. for use in connection with an interface to a user and/or an interface to a programming device. In some hearing aids, the output unit may comprise an output transducer, such as e.g. a loudspeaker for providing an air-borne acoustic signal or a vibrator for providing a structure-borne or liquid-borne acoustic signal. In some hearing aids, the output unit may comprise one or more output electrodes for providing electric signals (e.g. to a multi-electrode array) for electrically stimulating the cochlear nerve (cochlear implant type hearing aid).

In some hearing aids, the vibrator may be adapted to provide a structure-borne acoustic signal transcutaneously or percutaneously to the skull bone. In some hearing aids, the vibrator may be implanted in the middle ear and/or in the inner ear. In some hearing aids, the vibrator may be adapted to provide a structure-borne acoustic signal to a middle-ear bone and/or to the cochlea. In some hearing aids, the vibrator may be adapted to provide a liquid-borne acoustic signal to the cochlear liquid. e.g. through the oval window. In some hearing aids, the output electrodes may be implanted in the cochlea or on the inside of the skull bone and may be adapted to provide the electric signals to the hair cells of the cochlea, to one or more hearing nerves, to the auditory brainstem, to the auditory midbrain, to the auditory cortex and/or to other parts of the cerebral cortex.

A hearing aid may be adapted to a particular user's needs, e.g. a hearing impairment. A configurable signal processing circuit of the hearing aid may be adapted to apply a frequency and level dependent compressive amplification of an input signal. A customized frequency and level dependent gain (amplification or compression) may be determined in a fitting process by a fitting system based on a user's hearing data, e.g. an audiogram, using a fitting rationale (e.g. adapted to speech). The frequency and level dependent gain may e.g. be embodied in processing parameters, e.g. uploaded to the hearing aid via an interface to a programming device (fitting system), and used by a processing algorithm executed by the configurable signal processing circuit of the hearing aid.

A 'hearing system' refers to a system comprising one or two hearing aids, and a 'binaural hearing system' refers to a system comprising two hearing aids and being adapted to cooperatively provide audible signals to both of the user's ears. Hearing systems or binaural hearing systems may further comprise one or more 'auxiliary devices', which communicate with the hearing aid(s) and affect and/or benefit from the function of the hearing aid(s). Such auxiliary devices may include at least one of a remote control, a remote microphone, an audio gateway device, an entertainment device, e.g. a music player, a wireless communication device. e.g. a mobile phone (such as a smartphone) or a tablet or another device, e.g. comprising a graphical interface. Hearing aids, hearing systems or binaural hearing systems may e.g. be used for compensating for a hearing-impaired person's loss of hearing capability, augmenting or protecting a normal-hearing person's hearing capability and/or conveying electronic audio signals to a person. Hearing aids or hearing systems may e.g. form part of or interact with public-address systems, active ear protection systems, handsfree telephone systems, car audio systems, entertainment (e.g. TV, music playing or karaoke) systems, teleconferencing systems, classroom amplification systems, etc.

Embodiments of the disclosure may e.g. be useful in applications such as binaural hearing aid systems, e.g. hearing systems. e.g. hearables, comprising two earpieces, such as earphones, headsets and hearing aids.

BRIEF DESCRIPTION OF DRAWINGS

The aspects of the disclosure may be best understood from the following detailed description taken in conjunction with the accompanying figures. The figures are schematic and simplified for clarity, and they just show details to improve the understanding of the claims, while other details are left out. Throughout, the same reference numerals are used for identical or corresponding parts. The individual features of each aspect may each be combined with any or all features of the other aspects. These and other aspects, features and/or technical effect will be apparent from and elucidated with reference to the illustrations described hereinafter in which:

The figures are schematic and simplified for clarity, and they just show details which are essential to the understanding of the disclosure, while other details are left out. Throughout, the same reference signs are used for identical or corresponding parts.

Further scope of applicability of the present disclosure will become apparent from the detailed description given hereinafter. However, it should be understood that the detailed description and specific examples, while indicating preferred embodiments of the disclosure, are given by way of illustration only. Other embodiments may become apparent to those skilled in the art from the following detailed description.

DETAILED DESCRIPTION OF EMBODIMENTS

The detailed description set forth below in connection with the appended drawings is intended as a description of various configurations. The detailed description includes specific details for the purpose of providing a thorough understanding of various concepts. However, it will be apparent to those skilled in the art that these concepts may be practiced without these specific details. Several aspects of the apparatus and methods are described by various blocks, functional units, modules, components, circuits, steps, processes, algorithms, etc. (collectively referred to as "elements"). Depending upon particular application, design constraints or other reasons, these elements may be implemented using electronic hardware, computer program, or any combination thereof.

The electronic hardware may include micro-electronic-mechanical systems (MEMS), integrated circuits (e.g. application specific), microprocessors, microcontrollers, digital signal processors (DSPs), field programmable gate arrays (FPGAs), programmable logic devices (PLDs), gated logic, discrete hardware circuits, printed circuit boards (PCB) (e.g. flexible PCBs), and other suitable hardware configured to perform the various functionality described throughout this disclosure, e.g. sensors, e.g. for sensing and/or registering physical properties of the environment, the device, the user, etc. Computer program shall be construed broadly to mean instructions, instruction sets, code, code segments, program code, programs, subprograms, software modules, applications, software applications, software packages, routines, subroutines, objects, executables, threads of execution, procedures, functions, etc., whether referred to as software, firmware, middleware, microcode, hardware description language, or otherwise.

The present application relates to the field of hearing devices, e.g. hearing aids.

FIG. 1 shows a hearing system comprising two identically looking (or close to identically looking) hearing instruments (HD1, HD2) located in the respective ear canals of a user (U). Automatically, and seamlessly determining in which ear hearing devices, e.g. hearing aids, are mounted is not easy because the two ears are very symmetric. There is however one asymmetric cue, which we may take advantage of. If we measure the heartbeat (pulse) at each ear, we will see that the pulse typically arrives a little earlier at the left ear ('L-Ear' in FIG. 1) compared to the right ear ('R-Ear' in FIG. 1) of a user (U) (or the opposite (that the pulse arrives at the right ear before at the left ear)). This is illustrated in FIG. 2A, 2B.

Figure 2A:
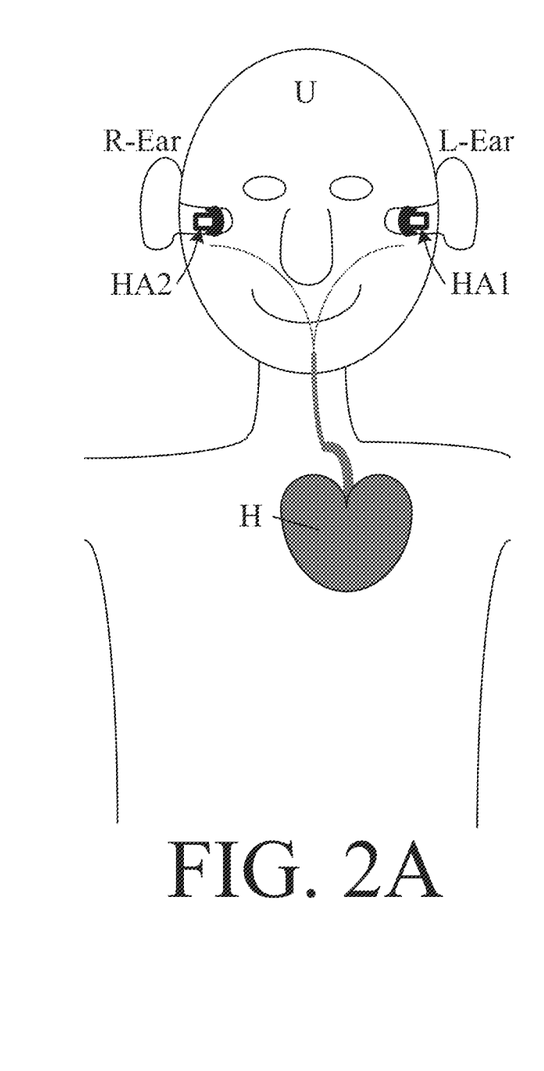
Figure 2B:
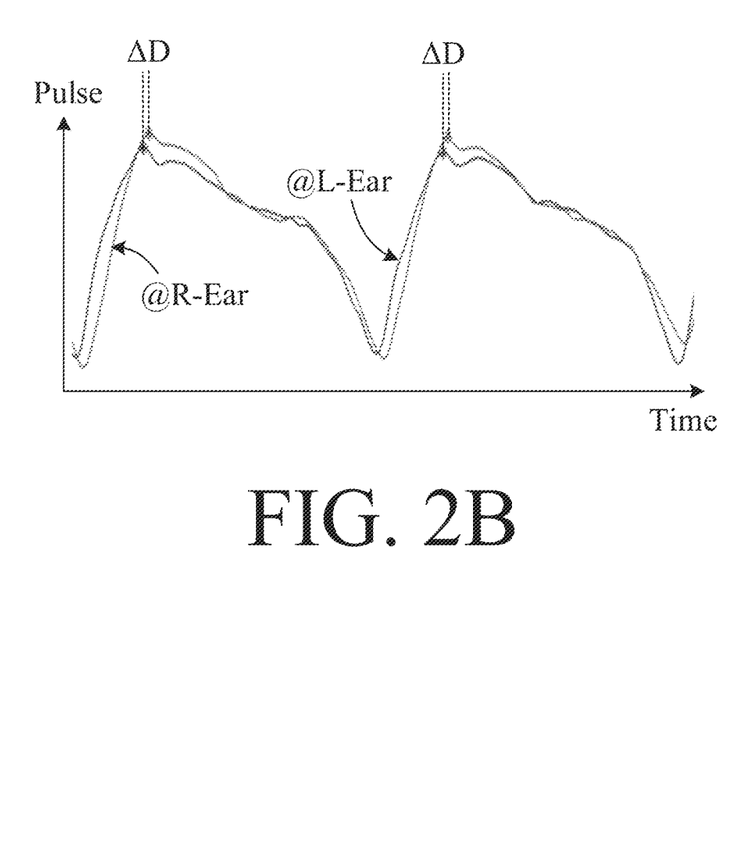
FIG. 2B shows respective heartbeat measurements (cardiogram) at left and right ears of a user illustrating that the pulses from a user's heart do not arrive at the same time at the two ears.

FIG. 2A shows a hearing system as shown in FIG. 1, but also including the user's heart (H) and schematic blood paths from the heart to the ears (L-Ear, R-Ear) of the user (U). FIG. 2B shows respective heartbeat measurements (cardiograms) versus time (Time) measured at left and right ears of a user illustrating that that the pulses from a user's heart (H) do not arrive at the same time at the two ears. Typically, the pulse arrives a little earlier at the left ear (@L-Ear) compared to the right ear (@R-Ear). The side can be determined by comparing the delay ($\Delta D$) between the measured pulses (e.g. by correlating the pulses or by comparing the peak time of the two pulse estimates, e.g. averaged over a number of pulses, e.g. 2-10 pulses). This requires that the pulse can be measured at each ear and exchanged between the two instruments. A pulse may be measured by an in-ear microphone (e.g. facing the eardrum. e.g. in a residual volume between an in the ear (ITE) part of the hearing aid and the eardrum). An in-ear microphone recording is, however, disturbed by other sounds, and it may thus take longer time to estimate the pulse signal. Preferably, the pulse may be obtained from a pulse oximetry sensor. e.g. a PPG sensor (PPG=Photoplethysmography) in each ear (regarding the use of pulse oximetry sensors in hearing aids, see e.g. US20190174238A1). The PPG sensor provides a less noisy estimate of the pulse independent of the surrounding sounds, and the measurement can be initiated as soon as the hearing devices are mounted at the ears. As a third option an in-car accelerometer may as well pick up the heartbeat. However, this measurement may require that the user is not moving as movements may add noise to the heartbeat measurements. On the other hand, as a PPG signal as well may be polluted by e.g. jaw movements, a measured acceleration signal may be used as a noise estimate in order to remove noise from a PPG measurements or used to qualify whether a PPG estimate is reliable. Any combination of PPG, microphone and accelerometer sensor data may be utilized to estimate the pulse. Alternatively, or additionally, the pulse may be picked up by vibrations measured by an in-ear accelerometer. The pulse may as well be determined from a combination of the mentioned sensors.

As not all users have their left-ear pulse arriving before the right ear pulse. The pulse arrival order may be measured e.g. during the first time the devices are mounted in the ears. During this initial fitting, it may be necessary by the user to indicate the correct ear.

Figure 3A:
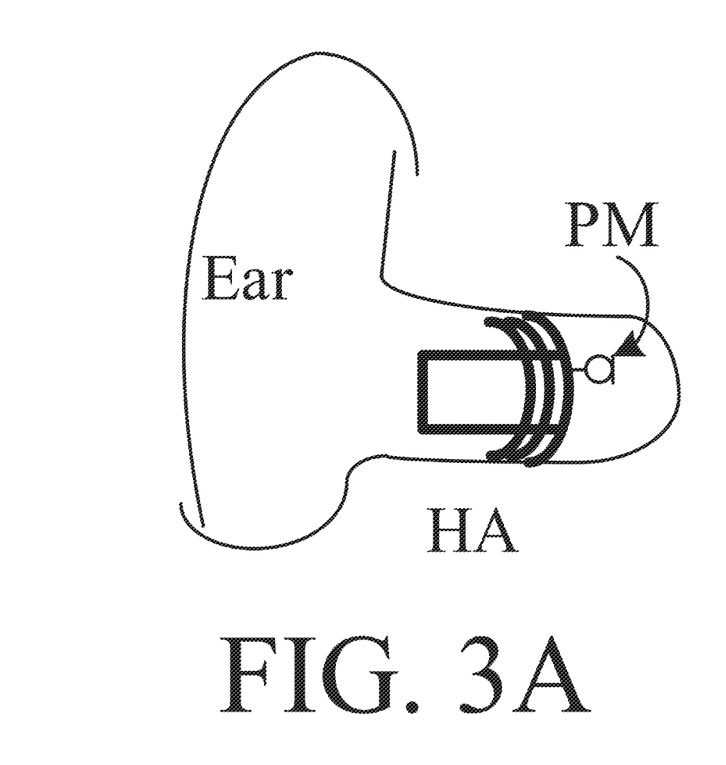
FIG. 3A shows a hearing device comprising a pulse sensor in the form of a microphone in the ear canal.
Figure 3B:
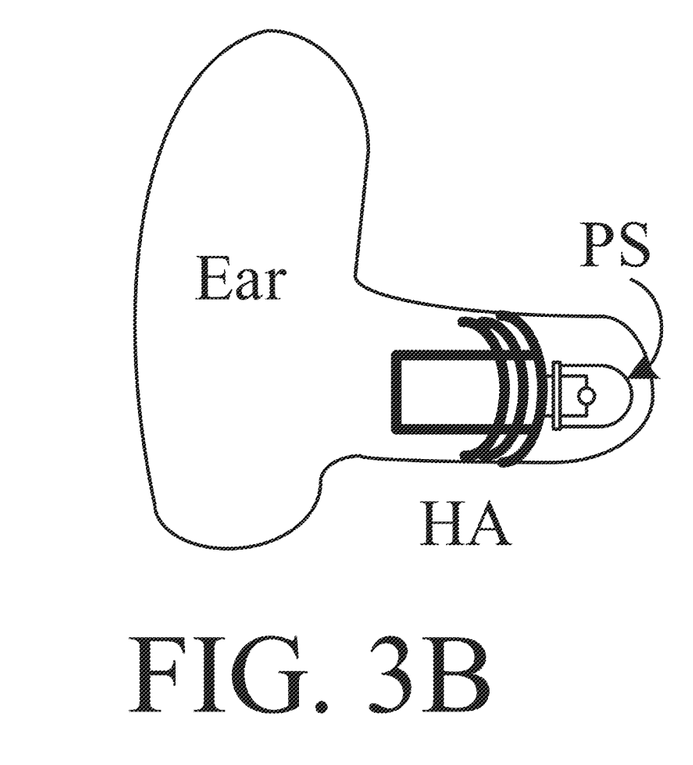
FIG. 3B shows a hearing device comprising a pulse sensor in the form of a light sensitive sensor, e.g. a PPG sensor.

FIG. 3 shows a hearing device comprising a pulse sensor in the form of a microphone in the ear canal, and FIG. 3B shows a hearing device comprising a pulse sensor in the form of a light sensitive sensor, e.g. a PPG sensor. FIGS. 3A and 3B illustrate the location of a microphone (PM) and a light sensitive sensor (PS) in a residual volume between an earpiece and the ear drum of the user. The microphone (PM) may e.g. be a conventional microphone or a dedicated low-frequency microphone for picking up vibrations introduced by the heartbeat, e.g. a movement sensor such as an accelerometer. The light sensitive sensor (PS) may e.g. be a e.g. a PPG sensor (e.g. pulse oximeter sensor combined with a heart rate sensor implemented by a PPG sensor). The hearing device, e.g. a hearing aid, comprises an earpiece configured to be located in an ear canal of the user. In the embodiments of FIG. 3A, 3B, the earpiece comprises guiding elements (e.g. a dome-like structure) for guiding and appropriately locating (e.g. centering) and/or sealing the earpiece in the ear canal. The earpiece may be sealed towards the walls of the ear canal to avoid unintentional exchange of air between the residual volume and the environment. The earpiece may comprise one or more venting channels for controlling such exchange. Thereby the conditions for picking up the heartbeat signals using a microphone are improved.

Figure 4:
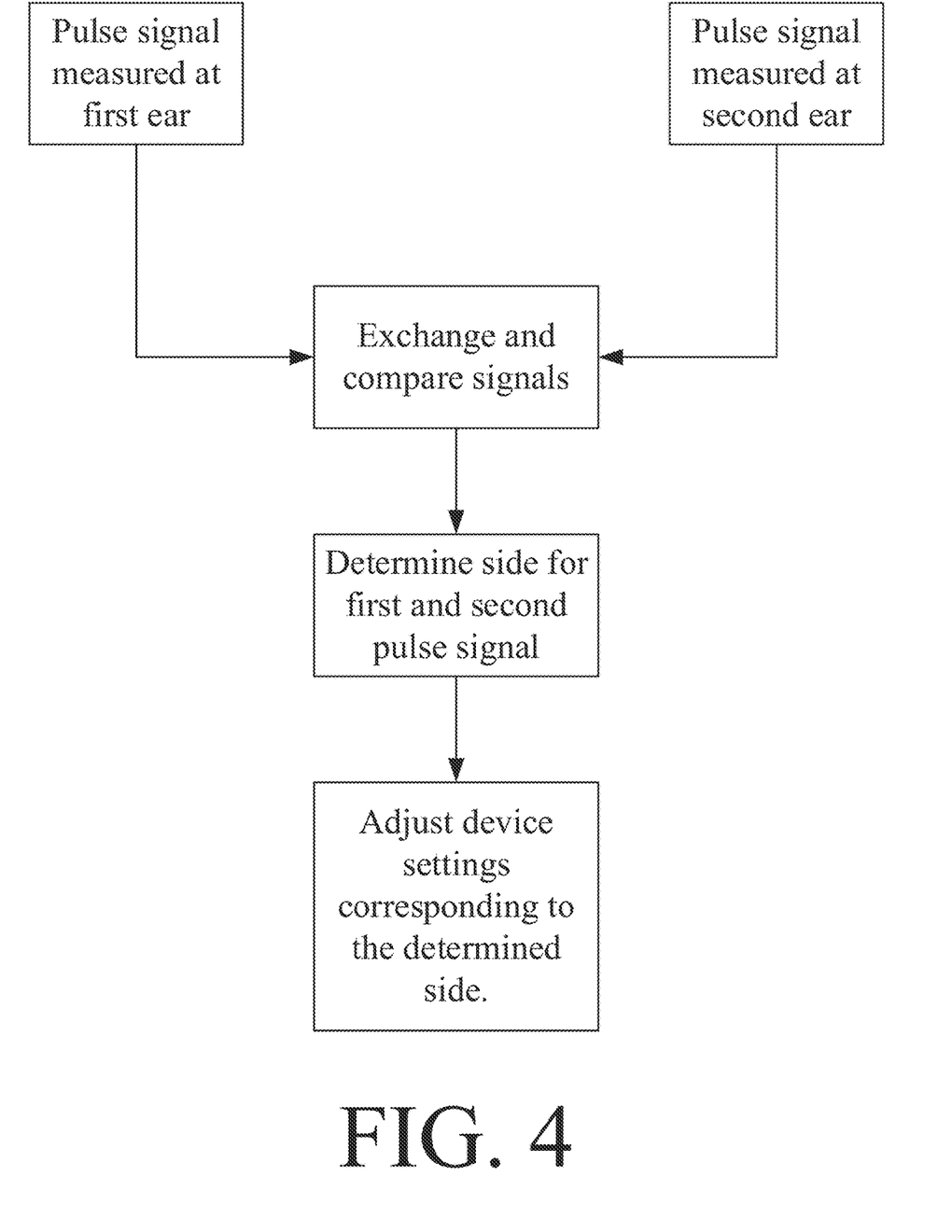
FIG. 4 shows a flow diagram for a scheme for determining side-dependent settings of a binaural hearing system.

FIG. 4 shows a flow diagram for a scheme for determining side-dependent settings of a binaural hearing system. Before the measurements can be initiated, the pulse should be detected at both ears (e.g. in a calibration procedure).

When the side has been determined the side-dependent settings can be set in each device. Side dependent settings could e.g. be Correct side while playing music, movie playback, or gaming.
3D rendering, e.g. 7.1 downmix.
Correct positioning of sound sources in augmented hearing.
Hearing loss compensation gain.
User interface, e.g. volume up by tapping left device, volume down by tapping right device
Sound Direction-of-arrival estimation
Or alternatively tell the user to swap the two devices.

This may be advantageous for hearables, for example, to automatically identify the right and left sides (and thus the correct side for audio playback).

For hearing aids, where the sound in one ear may be amplified more than the sound presented to the other ear, it may be beneficial to mute the devices until the correct side is identified in order to avoid unwanted loud sounds in the better ear. For less critical applications such as playing music via the instrument, the measurement can be performed during use. When the device is mounted, the side settings may be initialized based on selected side, from the previous mounting.

In principle, the side may be determined without exchanging any signals. Based on previous pulse recordings (data), the unique shape of a left-ear pulse and a right-ear pulse may be recognized (e.g. by use of a neural network). Such a recognition of a unique pulse shape may as well be used to uniquely identify the person using the hearing device (e.g. to unlock the hearing device or to unlock devices connected to the hearing device, e.g. as mentioned in our co-pending European patent application EP3709115A1.

Preferably, the comparison between pulse requires alignment of the clock in the two hearing instruments. However, the clock related to the pulse signal could be aligned based on the comparison of the delay between the audio signals in the different devices. External audio will typically arrive at the two ears within less than a millisecond. As the interaural pulse time differences are significantly higher than the interaural sound time difference, the interaural pulse signals can based on the exchanged audio signals be aligned with an accuracy of about 1 millisecond, which should be sufficient to estimate in which instrument the pulse arrives first.

The method may be applicable for devices such as hearing aids and hearables, in-ear devices, receiver-in the-ear devices, hearing devices for single channel deafness (where audio is transmitted from the bad ear to the good ear).

In a special embodiment, e.g. where a set of earbuds is shared between two people (listening to the same piece of music), it may be advantageous to detect that the pulse measured in the two devices do not origin from the same person. In that case, a stereo audio signal may be downmixed to two mono audio signals. The in-ear devices (e.g. hearing aids or earbuds, etc.) may comprise a detector for detecting whether the pulses received from the left and right earpieces are synchronized. If not, the devices are used by different persons. Besides the mono down mixing, also health monitoring may be stalled in such 'shared case' (at least if the instrument not used by the user). Also, special features such as access to phone via a wake word or key word commands could be disabled in a device, which has been shared with another user.

Figure 5:
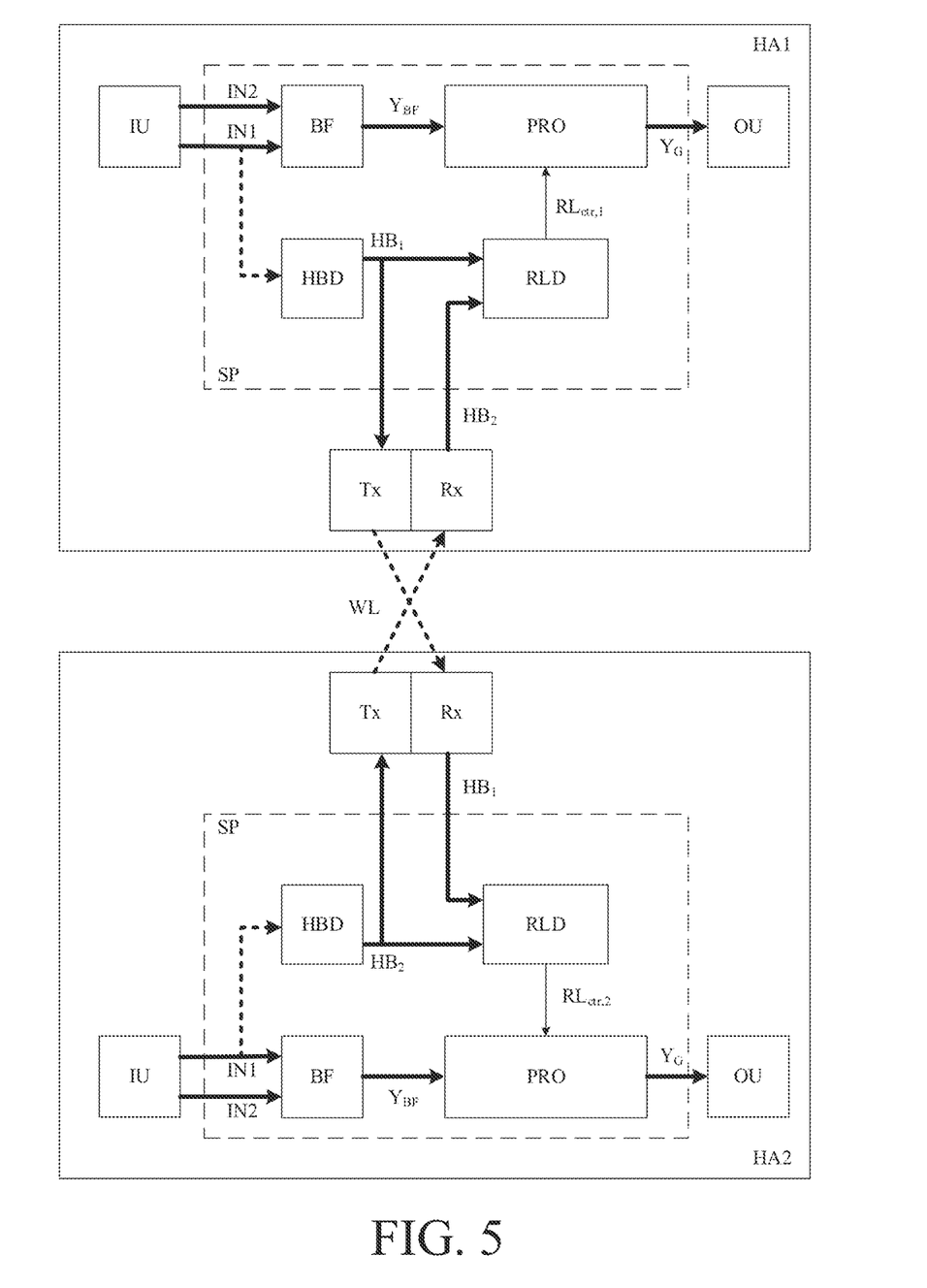
FIG. 5 shows an embodiment of a binaural hearing system according to the present disclosure.

FIG. 5 shows an embodiment of a binaural hearing system according to the present disclosure. The binaural hearing system of FIG. 5 may e.g. represent a binaural hearing aid system comprising first and second hearing aids (HA1, HA2). Each of the hearing aids are configured to be located at or in an ear of a user. The first and second hearing aids may comprise (or be constituted by) first and second earpieces configured to (e.g. customized to) be located at or in left and right ears of the user. The first and second hearing aids (e.g. the first and second earpieces) may be equal from their outer presentation (or at least difficult to differentiate). The first and second hearing aids may, however, comprise different functionality, e.g. embodied in different processing algorithms, or different settings (processing parameters) of such algorithms. The differences may e.g. reflect different compensation schemes of different hearing impairments of the user's left and right ears. The differences may e.g. reflect different functional tasks of the left and right hearing aids, e.g. one comprising more processing tasks than the other (e.g. related to wireless communication, or to binaural processing, etc.). Each hearing aid comprises a heartbeat detector (HBD) providing a pulse control signal ($HB_1$, $HB_2$). The pulse control signal may e.g. comprise a time dependent waveform of the heartbeat of the user. The heartbeat detector (HBD) may comprise a microphone, a movement sensor, or a PPG sensor. Each hearing aid comprises a processor (SP). The processor (SP) is configured to estimate whether the hearing aid is located at a left or a right ear of the user in dependence of the pulse control signal ($HB_1$, $HB_2$). Each of the hearing aids (HA1, HA2) comprises transceiver circuitry (Tx/Rx) configured to establish a communication link (WL), e.g. a wireless communication link, to another device. e.g. to the contra-lateral hearing aid of a binaural hearing aid system (here comprising the two hearing aids HAL, HA2). The 'another device' may e.g. be an auxiliary device. e.g. a remote control device, e.g. a smartphone or the like. The processor is configured to transmit the pulse control signal to the respective other device via the communication link (here from HA1 to HA2 and from HA2 to HA1, cf. signals $HB_1$ in HA2 and $HB_2$ in HA1). The processor (SP) may be configured to exchange the pulse control signals ($HB_1$, $HB_2$) between them in dependence of a trigger event, e.g. a power up of the first and second hearing aids of the binaural hearing aid system. A trigger event may alternatively or additionally be a request from a user interface.

Each of the hearing aids (HA1, HA2). e.g. the processor (SP), may comprise a right-left-detector (RLD) configured to provide a right-left control signal ($RL_{ctr,1}$, $RL_{ctr,1}$) indicative of whether the hearing aid in question is intended for location at the left or right ear of the user. Each hearing aid (e.g. the right left detector) may comprise a memory indicating a reference value for the comparison of (e.g. the difference between) the left and right pulse control signals ($HB_1$, $HB_2$) for the left and right ear of the user. The right left detector (RLD) may provide the right-left control signal ($RL_{ctr,1}$, $RL_{ctr,1}$) in dependence of the left and right pulse control signals ($HB_1$, $HB_2$) and the stored reference value for the hearing aid in question. The right-left control signal ($RL_{ctr,1}$, $RL_{ctr,1}$) is fed to a signal processor (PRO) of the hearing aid in question.

Each hearing aid comprises a forward path for processing an input sound captured by an input unit (IU) and providing stimuli that are perceivable to the user as sound (originating from the input sound) when presented to the user via an output unit (OU). The input unit (IU) may comprise one or more input transducers, e.g. microphones, each providing an electric input signal representing the input sound. The input unit (IU) may comprise one or more analogue to digital converters and analysis filter banks as appropriate for the application in question. In the embodiment of FIG. 3, each hearing aid (HA1, HA2) comprises a beamformer (BF) for providing a spatially filtered signal ($Y_{BF}$) based on two electric input signals (IN1, IN2). Each hearing aid comprises a signal processor (PRO) forming part of the forward path and is configured to process an input signal (here the spatially filtered (beamformed) signal ($Y_{BF}$)) and to provide a processed signal $Y_G$. The processed signal ($Y_G$) may e.g. be provided by applying a frequency and/or level dependent gain to the spatially filtered signal ($Y_{BF}$). The processed signal ($Y_G$) is fed to the output unit (OU). The output unit (OU) may comprise a synthesis filter bank and/or a digital to analogue converter as appropriate for the application in question.

The signal processor (PRO) may be configured to automatically select an appropriate processing parameter setting (e.g. from a memory) in dependence of right-left pulse control signal control signal ($RL_{ctr,1}$, $RL_{ctr,1}$) for the hearing aid in question. Each hearing aid may e.g. comprise a memory storing processing parameters (settings) for the relevant processing algorithms that deviate from the left to the right ear of the user (e.g. corresponding to different hearing impairments at left and right ears of the user). Thereby the appropriate parameters settings can be chosen and used in any of the first and second hearing aids irrespective whether they are mounted at the left or right ears of the user.

Each hearing aid, e.g. the processor (SP), may be configured to issue an alarm in dependence of the right-left pulse control signal control signal ($RL_{ctr,1}$, $RL_{ctr,1}$) for the hearing aid in question, e.g. in case that the first and second hearing aids are indicated not to be located at their appropriate ears. The alarm may comprise an information to the user (or other person) in case that the first and second hearing aids are not located at their appropriate ears. The hearing aid may e.g. instruct the user to swap the first and second hearing aids between the ears of the user (in case the processing parameters cannot be readily adapted to the intended values in the two hearing aids). Such alarm or information of instruction may e.g. be provided via a user interface, an audio and/or visual interface, e.g. via a loudspeaker of the hearing devices, or a remote control, and/or a smartphone, etc.

The hearing aids (HA1, HA2) may be constituted by or comprise an air-conduction type hearing aid, a bone-conduction type hearing aid, a cochlear implant type hearing aid, or a combination thereof.

A part of the processing of the two hearing aids of the binaural hearing aid system may be executed in a separate (e.g. portable) processing device. Some or all of the tasks of the respective processors of the first and second hearing aids of the binaural hearing aid system may be executed in the separate processing device. In that case the binaural hearing aid system comprises first and second earpieces adapted for being located at or in left and right ears of the user and a common external (e.g. portable) processing device. Each of the earpieces may comprise the respective input and output units (IU. OU) and the transceiver circuitry (Tx/Rx) of the embodiment of FIG. 5. The binaural hearing aid system may e.g. be configured to allow communication between the first and second earpieces and the separate processing device. The separate processing device may comprise transceiver circuitry corresponding to (or equivalent to) the transceiver circuitry (Tx/Rx) of the first and second earpieces to allow an appropriate exchange of data between them. The transceiver circuitry (Tx/Rx) may e.g. be implemented to support an appropriate (standardized or proprietary, preferably low latency) communication protocol, e.g. Bluetooth or UWB.

In an embodiment, the processing of the audio signals in the forward path of the first and second hearing aids (cf. e.g. units IU. BF, PRO and OU of each hearing aid of FIG. 5), and possibly the heartbeat detector (HBD), is implemented in the respective earpieces (hearing aids), whereas the comparison of the respective first and second pulse control signals ($HB_1$, $HB_2$) and determination of respective resulting control signals ($RL_{ctr,1}$, $RL_{ctr,2}$) is performed in the external processing device (e.g. handled by a user interface, e.g. implemented as an APP, of a smartphone or other portable device). Thereby, only the respective first and second pulse control signals ($HB_1$, $HB_2$) and the respective resulting first and second control signals ($RL_{ctr,1}$, $RL_{ctr,2}$) are exchanged between the first and second earpieces (hearing aids) and the external processing device.

It is intended that the structural features of the devices described above, either in the detailed description and/or in the claims, may be combined with steps of the method, when appropriately substituted by a corresponding process.

As used, the singular forms "a," "an," and "the" are intended to include the plural forms as well (i.e. to have the meaning "at least one"), unless expressly stated otherwise. It will be further understood that the terms "includes." "comprises," "including," and/or "comprising," when used in this specification, specify the presence of stated features, integers, steps, operations, elements, and/or components, but do not preclude the presence or addition of one or more other features, integers, steps, operations, elements, components, and/or groups thereof. It will also be understood that when an element is referred to as being "connected" or "coupled" to another element, it can be directly connected or coupled to the other element but an intervening element may also be present, unless expressly stated otherwise. Furthermore, "connected" or "coupled" as used herein may include wirelessly connected or coupled. As used herein, the term "and/or" includes any and all combinations of one or more of the associated listed items. The steps of any disclosed method are not limited to the exact order stated herein, unless expressly stated otherwise.

It should be appreciated that reference throughout this specification to "one embodiment" or "an embodiment" or "an aspect" or features included as "may" means that a particular feature, structure or characteristic described in connection with the embodiment is included in at least one embodiment of the disclosure. Furthermore, the particular features, structures or characteristics may be combined as suitable in one or more embodiments of the disclosure. The previous description is provided to enable any person skilled in the art to practice the various aspects described herein. Various modifications to these aspects will be readily apparent to those skilled in the art, and the generic principles defined herein may be applied to other aspects. The embodiments of the present disclosure have been illustrated by the example of hearing aids. The principles of the present disclosure may, however, equally well be useful in applications such as hearing systems (e.g. hearables) comprising two earpieces (for being located at or in respective left and right ears of a user), such as earphones or headsets or earpieces comprising health-related sensors for monitoring the user's present condition, etc. A hearing aid comprises a forward path from an (acoustic) input transducer (e.g. a microphone) to an output unit (e.g. an output transducer, such as a loudspeaker or a vibrator, etc.). Other hearing devices, e.g. headsets, earphones, hearables, etc. may e.g. comprise a first signal path from a wired or wireless audio receiver (providing audio from another location or streamed audio from an audio delivery device) to an output transducer (e.g. a loudspeaker) for being played for the user. Such device (e.g. embodied in a headset) may additionally comprise a second signal path from an input transducer for picking up sound from the environment of the device (e.g. the user's voice) to an output unit for transmitting (a possibly processed version) to another device or system. Any such hearing device comprising two (identically appearing) earpieces may benefit from the present scheme for identifying a left and right side of the user. Hence the hearing aid or hearing aid system described above might as well embody any of the hearing devices mentioned (or systems based thereon).

The left-right detection using heartbeat detection at left and right ears of a ser may be based on a combination with other methods as well, such as in combination with the detection of head movements (e.g. using an accelerometer and/or a gyroscope in the respective devices located at left and right ears of the user). In case a user turns the head, the y-axis of an accelerometer will have different direction (whereby the side can be detected). Thereby an increased reliability of the left-right indication can be achieved.

The claims are not intended to be limited to the aspects shown herein but are to be accorded the full scope consistent with the language of the claims, wherein reference to an element in the singular is not intended to mean "one and only one" unless specifically so stated, but rather "one or more." Unless specifically stated otherwise, the term "some" refers to one or more.

Accordingly, the scope should be judged in terms of the claims that follow.

REFERENCES

EP2991380A1 (Oticon) Mar. 2, 2016
US20190174238A1 (Oticon) Jun. 6, 2019
EP3709115A1 (Oticon) Sep. 6, 2020

The invention claimed is:

1. A hearing aid configured to be located at or in a first ear of a user, the hearing aid comprising
   a heartbeat detector providing a pulse control signal indicative of a time variation of said user's heartbeat at said first ear of the user, and
   a processor,
       wherein the hearing aid is configured receive a second pulse control signal from a second hearing aid configured to be located at or in a second ear of the user, wherein said second pulse control signal is indicative of a time variation of said user's heartbeat at said second ear of the user;
       wherein the processor is configured to estimate whether said hearing aid is located at a left or a right ear of the user in dependence of said pulse control signal and said second pulse control signal;
       wherein the hearing aid is configured to perform the estimating of whether said hearing aid is located at a left or a right ear of the user in response to a specific criterion, which relates to the reliability of the pulse control signal, being fulfilled; and
       wherein the specific criterion comprises any one or combination of the following:
           the user is not moving,
           the user is not talking, and
           background noise is not above a predetermined level.

2. A hearing aid according to claim 1 comprising transceiver circuitry configured to establish a communication link to another device.

3. A hearing aid according to claim 1 wherein the pulse control signal comprises a time dependent waveform of the heartbeat of the user.

4. A hearing aid according to claim 1 wherein said processor is configured to transmit said pulse control signal to another device.

5. A hearing aid according to claim 1 wherein said heartbeat detector comprises a microphone, a movement sensor, or a PPG sensor.

6. A hearing aid according to claim 1 wherein said processor is configured to automatically select appropriate processing parameters in dependence of said pulse control signals.

7. A hearing aid according to claim 1 wherein said processor is configured to issue an alarm in case that the hearing aid is not located at its appropriate ear.

8. A hearing aid according to claim 1 configured to monitor changes in timing of the pulse control signal.

9. A hearing aid according to claim 1 being constituted by or comprising an air-conduction type hearing aid, a bone-conduction type hearing aid, a cochlear implant type hearing aid, or a combination thereof.

10. A binaural hearing aid system comprising first and second hearing aids according to claim 1 configured to exchange said pulse control signals between them.

11. A binaural hearing aid system according to claim 10 configured to exchange said pulse control signals between them in dependence of a trigger event.

12. A binaural hearing aid system according to claim 10 further comprising or being configured to communicate with an auxiliary device.

13. A binaural hearing aid system according to claim 12 comprising a user interface implemented as a software application executed on the auxiliary device.

14. A binaural hearing aid system according to claim 10 configured to provide that the determination of whether a given one of the first and second hearing aids is located at a left or a right ear of the user in dependence of the first and second pulse control signals is performed in an auxiliary device.

15. Use of a hearing aid according to claim 1.

16. A method of operating a hearing aid configured to be located at or in a first ear of a user, the method comprising
    providing a first pulse control signal indicative of a time variation of said user's heartbeat at said ear of the user,
    receiving a second pulse control signal from a second hearing aid configured to be located at or in a second ear of the user, wherein said second pulse control signal is indicative of a time variation of said user's heartbeat at said second ear of the user, and
    estimating whether said hearing aid is located at a left or a right ear of the user in dependence of said first and second pulse control signals,
        wherein the estimating of whether said hearing aid is located at a left or a right ear of the user is performed in response to a specific criterion, which relates to the reliability of the pulse control signal, being fulfilled; and wherein the specific criterion comprises any one or combination of the following:
- the user is not moving,
- the user is not talking, and
- background noise is not above a predetermined level.

17. A method according to claim 16 comprising transmitting said first pulse control signal to a second hearing aid configured to be located at a second ear of the user.

18. A method according to claim 16 comprising providing that the determination of whether the hearing aid is located at a left or a right ear of the user is performed in a separate device in communication with the hearing aid.

* * * * *